US011541246B2

(12) United States Patent
Cordero Alvarez et al.

(10) Patent No.: US 11,541,246 B2
(45) Date of Patent: Jan. 3, 2023

(54) DEVICE AND METHOD FOR DETECTING VENTRICULAR FIBRILLATION

(71) Applicant: SORIN CRM SAS, Clamart (FR)

(72) Inventors: Rafael Cordero Alvarez, Paris (FR); Delphine Feuerstein, Boulogne Billancourt (FR)

(73) Assignee: Sorin CRM SAS, Clamart (FR)

( * ) Notice: Subject to any disclaimer, the term of this patent is extended or adjusted under 35 U.S.C. 154(b) by 376 days.

(21) Appl. No.: 16/721,534

(22) Filed: Dec. 19, 2019

(65) Prior Publication Data

US 2020/0197715 A1 Jun. 25, 2020

(30) Foreign Application Priority Data

Dec. 20, 2018 (FR) ...................................... 1873536

(51) Int. Cl.
A61N 1/39 (2006.01)
A61N 1/37 (2006.01)
(Continued)

(52) U.S. Cl.
CPC ............ *A61N 1/3956* (2013.01); *A61B 5/316* (2021.01); *A61N 1/046* (2013.01); *A61N 1/3684* (2013.01);
(Continued)

(58) Field of Classification Search
CPC .... A61B 2562/0219; A61B 2562/0247; A61B 5/1102; A61B 5/316; A61B 5/361;
(Continued)

(56) References Cited

U.S. PATENT DOCUMENTS 5,524,631 A 6/1996 Zahorian et al.
10,420,527 B2 * 9/2019 Misra ....................... A61B 7/00
(Continued)

FOREIGN PATENT DOCUMENTS

EP 1 622 679 A1 2/2006
EP 2 364 639 A1 9/2011
(Continued)

OTHER PUBLICATIONS

Beyramienanlou, Hamed et al., "An Efficient Teager Energy Operator-Based Automated QRS Complex Detection," Journal of Healthcare Engineering, vol. 2018, Sep. 18, 2018, pp. 1-11, XP055641559, Brentwood, ISSN: 2040-2295, DOI: 10.1155/2018/8360475.
(Continued)

*Primary Examiner* — Jon Eric C Morales
(74) *Attorney, Agent, or Firm* — Foley & Lardner LLP

(57) ABSTRACT

The present invention relates to a medical device, in particular to an implantable medical device, comprising at least one implantable or non-implantable hemodynamic sensor configured for detecting hemodynamic cardiac signals, a controller configured for processing and analyzing the detected cardiac hemodynamic signals or signals derived from the detected cardiac hemodynamic signals by applying to said signals a Teager Energy Operator (TEO). The controller further comprises at least one algorithm configured to determine the need for a defibrillation operation by taking into account the at least one output hemodynamic signal. The present invention also provides a method and software for detecting or treating a ventricular fibrillation episode by taking into account cardiac hemodynamic signals.

23 Claims, 7 Drawing Sheets

(51) Int. Cl.
*A61N 1/04* (2006.01)
*A61N 1/368* (2006.01)
*A61B 5/316* (2021.01)

(52) U.S. Cl.
CPC ........... *A61N 1/371* (2013.01); *A61N 1/3925* (2013.01); *A61B 2562/0219* (2013.01); *A61B 2562/0247* (2013.01)

(58) Field of Classification Search
CPC ....... A61B 5/363; A61B 5/686; A61B 5/7207; A61B 5/7282; A61N 1/046; A61N 1/3621; A61N 1/3684; A61N 1/371; A61N 1/3925; A61N 1/3956
See application file for complete search history.

(56) References Cited

U.S. PATENT DOCUMENTS

2004/0225332 A1 11/2004 Gebhardt et al.
2011/0098587 A1 4/2011 Haefner

FOREIGN PATENT DOCUMENTS

| | | |
|---|---|---|
| JP | 2003-204944 A | 7/2003 |
| JP | 2007-503280 A | 2/2007 |
| JP | 2016-182165 A | 10/2016 |

OTHER PUBLICATIONS

Office Action on FR Application No. 1873536 dated Nov. 27, 2019. 10 pages.
Oweis, Rami J. et al., "Heart Sounds Segmentation Utilizing Teager Energy Operator," Journal of Medical Imaging and Health Informatics, vol. 4, No. 4, Aug. 1, 2014, pp. 488-499, XP055642678, ISSN: 2156-7018, DOI: 10.1166/jmihi.2014.1292.
Weinberg, Louis et al., "Takahasi's Results on Tchebycheff and Butterworth Ladder Networks," IRE Transactions on Circuit Theory, Jun. 1960, pp. 88-101.
EP Office Action on EP Appl. Ser. No. 19214173.7 dated May 19, 2020 (7 pages).
JP Office Action on JP Appl. Ser. No. 2019-228166 dated Feb. 26, 2021, with English translation (19 pages).

* cited by examiner

DEVICE AND METHOD FOR DETECTING VENTRICULAR FIBRILLATION

CROSS-REFERENCE TO RELATED APPLICATION

This application claims the benefit of and priority to French Application No. 1873536, filed Dec. 20, 2018, which is incorporated herein by reference in its entirety.

BACKGROUND

The present invention relates to a medical device in particular to an implantable medical device, as well as to a method and software for detecting ventricular fibrillation.

Sudden cardiac death, caused by ventricular tachyarrhythmia, remains a leading cause of death in developed countries. The rapid detection of such episodes is of crucial importance to allow immediate response and the provision of appropriate treatment. The cardiac status of a survivor of a ventricular tachyarrhythmia is closely monitored at the hospital, usually with an ECG monitoring system. Monitoring cardiac activity for the detection of ventricular tachyarrhythmia generally involves the use of electrophysiological signals such as electrocardiograms (ECG) or electrograms (EGM). These signals provide electrical information of heart function and are used to detect the occurrence of ventricular tachyarrhythmia such as ventricular fibrillation.

While hospital-based ECG monitoring is a viable, short-term, cost-effective alternative, various long-term treatment options may be recommended for patients with sudden death cardiac risk. These treatment options include pharmacological treatment and/or implantation of a defibrillator. Implantable automatic defibrillators comprise electrodes that record EGMs. Subcutaneous implantable defibrillators are capable of recording ECGs. These EGMs/ECGs are processed by algorithms in the device to detect a heart rhythm that may indicate, for example, the presence of ventricular fibrillation. Nevertheless, these algorithms can give rise to false positives, often caused by other sources of electrophysiological noise. False positives correspond to the detection of phenomena such as electrical noise, myopotentials, double detection of a wide QRS, T-wave detection, supraventricular tachycardia or any other electrophysiological phenomenon that does not correspond to ventricular tachyarrhythmia, but that is inappropriately detected as such. Indeed, the frequent presence of electrophysiological background noise reduces the signal/noise ratio. In an implantable cardioverter defibrillator, for example, a false positive would result in appropriate shock, which can be traumatic or even deleterious by inducing a ventricular tachyarrhythmia.

US 2004/225332 A1 relates to a system and method for detecting and discriminating cardiac arrhythmias based on mechanical signals of cardiac wall motion and cardiac depolarization electrical signals. The algorithm of US2004/225332 A1 compares and corroborates the detected mechanical signals with the detected electrical signals to classify the heart rate. Thus, US 2004/225332 A1 uses, in addition to electrophysiological signals, cardiac mechanical activity signals for the detection of ventricular arrhythmia which is normally detected only from electrophysiological signals. However, the algorithm of US 2004/225332 A1 is not suitable for improving the detection of ventricular fibrillation because it is always based on electrophysiological signals that often give rise to false positives due to the presence of electrophysiological noise from other sources (e.g. due to myopotentials).

US 2011/0098587 A1 relates to the use of non-electrophysiological sensors such as accelerometers or acoustic transducers, in addition to a series of electrodes which detect electrophysiological signals, which are implanted subcutaneously to, among other things, detect a ventricular tachyarrhythmia. However, according to US 2011/0098587A1, recorded signals (by a subcutaneous accelerometer for example) that are non-electrophysiological signals are used to select the best possible output signal of a series of electrophysiological signals by a "Blind Signal Separation" process (BSS). The output signal resulting from the BSS is used to classify heart rhythms and detect, for example, ventricular tachyarrhythmias. Thus, the method of US 2011/0098587A1 is dependent on the electrophysiological signals for the classification of cardiac rhythms. However, such signals, if polluted by noise, such as myopotentials that are not suppressed during the separation process, can lead to the detection of false positives. Thus, the device of US 2011/0098587A1 is not suitable for improving the detection of ventricular fibrillation.

It is an object of the present invention to improve the discrimination specificity of a cardiac event, in particular ventricular fibrillation, and to reduce the occurrence of false positive detection results, i.e. the detection of phenomena such as electrical noise, myopotentials, double detection of wide QRS, T-wave sensing, supraventricular tachycardia, or any other electrophysiological phenomena that do not match ventricular tachyarrhythmia but are erroneously detected as such.

SUMMARY

The object of the present invention is achieved by a medical device, in particular an implantable medical device, comprising at least one implantable or non-implantable hemodynamic sensor configured to detect cardiac hemodynamic signals; a controller configured to process and analyze the detected hemodynamic cardiac signals and/or signals derived from the detected hemodynamic cardiac signals by applying to said signals a Teager Energy Operator (TEO) defined by: TEO $\{x\ (n)\}=\psi(n)=x^2(n-1)-x(n-2)\cdot x(n)$ wherein "x (n)" is a cardiac hemodynamic signal, "$\psi(n)$" is the output hemodynamic signal and "n" refers to a predetermined sample; said controller further comprising at least one algorithm configured to determine the need for a defibrillation operation taking into account the at least one output hemodynamic signal.

The mechanical energy generated by the heart during ventricular fibrillation is greatly reduced compared to that of a normal sinus rhythm. The device of the invention uses this fact to detect ventricular fibrillation episodes as a function of the detected hemodynamic signal(s) or their derived signals. Transformation by application of the TEO operator makes it possible to increase the signal-to-noise ratio of the output signals and thus provides a representation of the detected signals or of signals derived from the detected signals, from which it is easier to determine whether cardiac sounds are present or not (i.e. whether or not there is mechanical cardiac activity). Indeed, the processing of the signals by the TEO operator makes it possible to condense the sound of the heart essentially in a single peak.

With respect to false-positive results, the device of the invention is capable of performing electrophysiological signals relating to electrical activity for detecting ventricular fibrillation, such as electrocardiograms (ECGs) or electrograms (EGMs) which are usually used to detect tachyarrhythmia, but tend to produce false positive detection results, especially in the case of ventricular fibrillation. Thus, thanks to the TEO representation, the detection of ventricular fibrillation episodes can be performed more easily while reducing the occurrence of false positive detection results.

The present invention is relating to a medical device that can be further improved by the following embodiments.

According to one embodiment, the at least one hemodynamic sensor may be an implantable or non-implantable accelerometer, a microphone, a piezoelectric sensor or a pressure sensor capable of detecting hemodynamic cardiac signals, in particular cardiac sounds. An accelerometer is configured to detect hemodynamic heart signals and may be implanted either in the heart, subcutaneously, or externally attached to the skin. Hemodynamic sensors that can be used for the implementation of the device according to the present invention can thus be implantable or non-implantable (subcutaneous or cutaneous) sensors. As a result, the hemodynamic sensors can be located at different locations in and/or on the patient's body.

According to one embodiment, the at least one algorithm of the controller can be configured to determine the need for a defibrillation operation if at least one characteristic of the output hemodynamic signals does not exceed a predetermined threshold for a time duration that is greater than at a duration associated with an episode of ventricular fibrillation. In addition, the at least one characteristic of the output hemodynamic signal may be the amplitude, the energy, the average value or the median value, or the root mean square value of said signal. The invention thus relies on the absence of activity rather than on the presence of increased activity wherein electrophysiological noise artifacts could affect the cardiac mechanical activity signal. Moreover, even if similar mechanical artifacts were present in the signal, they would not give false positives.

According to one embodiment, the amplitude of the output hemodynamic cardiac signals, and/or the number of times that each of the output hemodynamic cardiac signals crosses in either increasing or decreasing order the predetermined threshold, and/or the number of peaks of each signal that exceeds the predetermined threshold during the predefined time period, may be taken into account in determining whether or not ventricular fibrillation is present. TEO processing allowing improving the sharpness of the signals, and therefore of the peaks, the determination of a ventricular fibrillation compared to a threshold is facilitated.

According to one embodiment, the medical device may further comprise a defibrillator, in particular an implantable defibrillator, configured to generate an electrical defibrillation signal, and at least one electrode connected to said defibrillator by a lead configured to deliver said electrical defibrillation signal to a patient when the need to trigger a defibrillation operation is determined by the controller of the medical device. Thus, the device is also configured to treat ventricular fibrillation following the detection of a ventricular fibrillation episode by a defibrillator.

According to one embodiment, the controller may be configured to determine the need of initiating a defibrillation operation by comparing the output hemodynamic signal signals with at least one independently detected electrophysiological signal to the cardiac hemodynamic signals by the at least one electrode. The fact of taking into account and comparing signals of different (electrophysiological and hemodynamic) natures, which are detected independently of one another makes it possible to verify and improve the reliability of the result (presence or absence of an episode of ventricular fibrillation).

According to one embodiment, the controller may be configured to determine the need for a defibrillation operation by taking into account only hemodynamic cardiac signals. The device can thus be freed from the detection and processing of electrophysiological signals, which simplifies the detection of ventricular fibrillation.

According to one embodiment, the controller may be configured to bandpass filter the detected cardiac hemodynamic signals and/or the signals derived from the detected hemodynamic cardiac signals in a range of 1 to 100 Hz, in particular from 7.5 to 49. Hz. The filtering of hemodynamic signals in this narrow band of frequencies eliminates the low frequency respiratory contributions and the contributions of high frequency acoustic heart waves. In addition, this limits the influence that motion artifacts could have on heart signals. This is particularly relevant when the patient implanted with such a device moves and, for example, is doing physical exercise.

According to one embodiment, the controller may further be configured to filter the output signals by applying a windowing function, in particular a Hamming window. The Hamming window makes it possible to make the peaks of the output signals larger with respect to the noise but also to facilitate the processing and the analysis of the output signals, because it reduces the risk of double detections (i.e. several peaks located close to each other and being possibly mistaken for a single peak).

According to one embodiment, the controller may be configured to determine the need for a defibrillation operation and/or to initiate a defibrillation operation according to a predefined static threshold, or according to a dynamic threshold periodically recalculated and derived from one or several characteristics of the cardiac hemodynamic signals or of their representation by the Teager Energy Operator. Thus, the value of the predetermined threshold may be a constant value, which is defined a priori. Alternatively, the dynamic threshold used to establish the presence or absence of ventricular fibrillation is more specific and thus makes it possible to refine the detection of the ventricular fibrillation episode.

The embodiments may be combined to form more advantageous alternative embodiments of the present invention.

The object of the present invention can also be achieved with a method for treating hemodynamic cardiac signals detected by at least one hemodynamic sensor of a medical device, in particular an implantable medical device, comprising at least one step of processing detected hemodynamic signals and/or signals derived from detected hemodynamic cardiac signals which comprises the application of a Teager Energy Operator (TEO) defined by: TEO $\{x(n)\}=\psi(n)=x^2(n-1)-x(n-2)\cdot x(n)$ wherein "x (n)" is a detected hemodynamic cardiac signal, "$\psi(n)$" is the output hemodynamic cardiac signal and "n" refers to a predetermined sample; and further comprising a step wherein the presence or absence of ventricular fibrillation is determined by taking into account the output hemodynamic cardiac signal(s) relative to a predetermined threshold.

The mechanical energy generated by the heart during a ventricular fibrillation is greatly reduced by comparison to that of a normal sinus rhythm. The method of the invention uses this fact to detect episodes of ventricular fibrillation depending on the detected hemodynamic cardiac signals or of their derived signals. Transformation by application of the TEO operator can increase the signal-to-noise ratio of the output signals and provides thus a representation of the detected signals or signals derived from the detected signals, from which it is easier to determine if heart sounds are present or not (i.e. whether or not there is an mechanical heart activity).

The present invention relating to a method can be further improved by the following embodiments.

With regard to false-positive results, the method of the invention is capable of performing electrophysiological signals relating to electrical activity to arrive at the detection of ventricular fibrillation, such as electrocardiograms (ECG) or electrograms (EGMs) that are usually used to detect tachyarrhythmia, but may result in false positive detection results, especially in the case of ventricular fibrillation. Thus, thanks to the TEO representation, the detection of ventricular fibrillation episodes can be performed more easily while reducing the occurrence of false positive detection results.

According to one embodiment, the signal processing step may be preceded by a signal preprocessing step at which the detected cardiac hemodynamic signals and/or the signals derived from the detected hemodynamic cardiac signals are bandpass filtered, in particular in a range of 1 to 100 Hz, more in particular from 75 to 49 Hz. The filtering of the hemodynamic signals in this narrow frequency band eliminates the low frequency respiratory contributions and the contributions of the acoustic heart waves with high frequency. In addition, this limits the influence that motion artifacts could have on heart signals. This is particularly relevant when the patient equipped and/or implanted with such a device moves and, for example, does physical exercise.

According to one embodiment, the signal processing step may be followed by a signal post-processing step at which the output hemodynamic signals are filtered by applying a windowing function, in particular by application of a Hamming window. The Hamming window makes it possible to make the peaks of the output signals larger with respect to the noise but also to facilitate the processing and the analysis of the output signals, because it reduces the risk of double detections (i.e. several peaks located close to each other and being possibly assimilated to a single peak).

According to one embodiment, the at least one hemodynamic sensor may be an implantable or non-implantable N-axis accelerometer (N≥1), a microphone, a piezoelectric sensor or a pressure sensor capable of detecting hemodynamic cardiac signals, especially heart sounds. An accelerometer is configured to detect hemodynamic cardiac signals and may be implanted either in the heart, subcutaneously, or externally attached to the skin.

According to one embodiment, the N cardiac signals detected by the N-axis accelerometer can be combined in a new signal along an axis N+1, the axis N+1 being determined so that the amplitude and/or the signal-to-noise ratio and/or the stability and/or a relevant physiological parameter of the new signal is maximum along the N+1 axis. In this manner, the signals can be combined to produce a different signal that is more patient-specific and/or that maximizes the properties of the detected hemodynamic signal, such as amplitude, signal-to-noise ratio, and/or stability.

According to one embodiment, the predetermined threshold may be a predefined static threshold, or a dynamic threshold, recalculated periodically and derived from one or more characteristics of the cardiac hemodynamic signals or from their representation by the Teager Energy Operator. Thus, the value of the predetermined threshold may be a constant value and which is defined a priori. Alternatively, the dynamic threshold used to establish the presence or absence of ventricular fibrillation is more specific and thus makes it possible to refine the detection of the ventricular fibrillation episode.

According to one embodiment, the amplitude, and/or the number of times that each of the output hemodynamic signals crosses in either ascending or descending order the predetermined threshold, and/or the number of peaks of each signal which exceeds the predetermined threshold during a predefined time lapse, can/may be taken into account to determine the presence or absence of ventricular fibrillation. The determination of a ventricular fibrillation with respect to a threshold is thus facilitated because the TEO processing has made it possible to improve the sharpness of the peaks, and therefore of the signals.

According to one embodiment, the presence or absence of ventricular fibrillation can be determined by taking into account only hemodynamic cardiac signals. The method can thus be freed from detection, processing and comparison with electrophysiological signals, thereby simplifying the method for detecting ventricular fibrillation.

Alternatively, the presence or absence of ventricular fibrillation can be established by comparing the output hemodynamic signal with at least one electrophysiological signal detected by an electrode of the medical device. The fact of taking into account and comparing signals of different natures (electrophysiological and hemodynamic) allows verifying and improving the reliability of the result (presence or absence of an episode of fibrillation ventricular).

The object of the present invention can also be achieved with cardiac hemodynamic signal processing software detected by at least one hemodynamic sensor of a medical device, in particular an implantable medical device, characterized in that it comprises instructions capable, when executed by the medical device, of performing the processing of the detected hemodynamic signals and/or signals derived from the detected hemodynamic cardiac signals by application of a Teager Energy Operator (TEO) defined by: TEO $\{x(n)\}=\psi(n)=x^2(n-1)-x(n-2)\cdot x(n)$ wherein "x (n)" is the detected hemodynamic signal, "$\psi(n)$" is the output signal and "n" refers to a predetermined sample; and comparing at least one characteristic of the output signal to a predetermined threshold; and triggering an alert when the at least one characteristic of the output signal does not exceed the predetermined threshold for a predefined period of time.

The mechanical energy generated by the heart during ventricular fibrillation is greatly reduced compared to that of a normal sinus rhythm. The software of the invention is based on this fact to detect ventricular fibrillation episodes as a function of the detected hemodynamic signal or of their derived signals. Transformation by the TEO operator makes it possible to increase the signal-to-noise ratio of the output signals and thus provides a representation of the original signals from which it is easier to determine whether cardiac sounds are present or not (i.e. whether or not there is a mechanical cardiac activity). In addition, unlike other methods and algorithms, such as wavelet filtering, the TEO operator does not require prior signal information or learning for the algorithm.

The present invention relating to software can be further improved by the following embodiments.

According to one embodiment, the software may further comprise the pre-processing of the detected hemodynamic cardiac signals and/or of signals derived from the cardiac hemodynamic signals detected by bandpass filtering, in particular in a range from 1 to 100 Hz, more particularly from 7.5 to 49 Hz. The pre-filtering of hemodynamic signals in this narrow frequency band eliminates low-frequency respiratory contributions as well as the contributions of high-frequency acoustic heart waves. In addition, this limits the influence that motion artifacts could have on cardiac signals. This is particularly relevant when the patient implanted with such a device moves and, for example, does physical exercise.

According to one embodiment, the software may further comprise the post-processing of the output signal by application of a windowing function, in particular a Hamming window. The Hamming window makes it possible to make the peaks of the output signals larger with respect to the noise but also to facilitate the processing and the analysis of the output signals, because it reduces the risk of double detections (i.e. several peaks located close to each other and being possibly assimilated to a single peak).

BRIEF DESCRIPTION OF THE DRAWINGS

The invention and its advantages will be explained in more detail in the following embodiments and relying in particular on the following accompanying figures, wherein.

DETAILED DESCRIPTION

The invention will now be described in more detail by using advantageous embodiments in an exemplary manner and with reference to the drawings. The described embodiments are simply possible configurations and it should be kept in mind that the individual characteristics as described above may be provided independently of each other or may be omitted altogether when implementing the present invention.

Figure 1A:
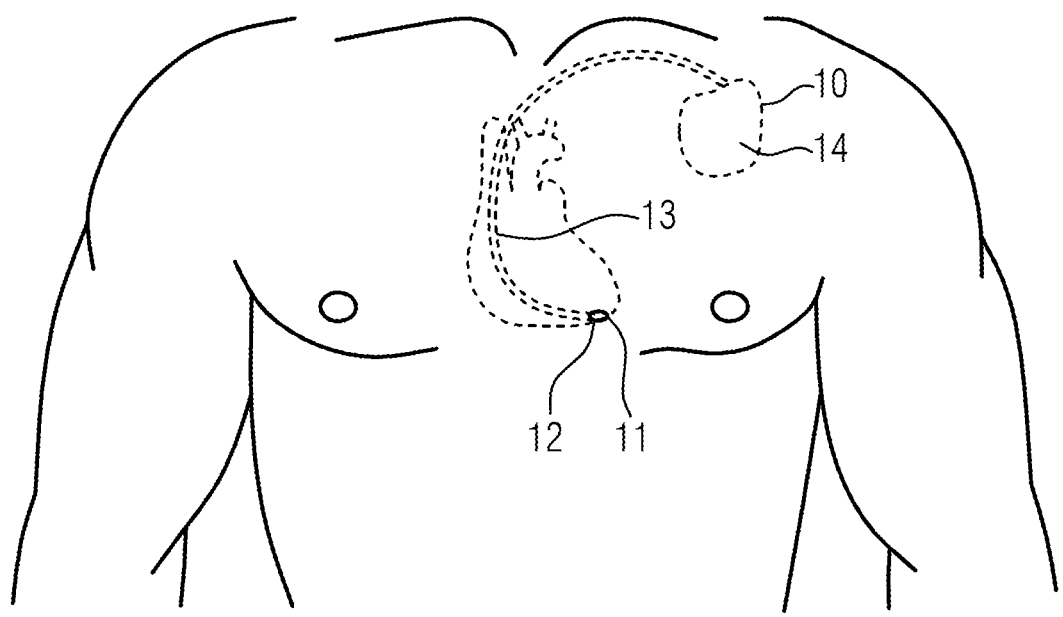
FIG. 1a represents a medical device comprising a hemodynamic cardiac sensor according to a first embodiment of the invention.
Figure 1B:
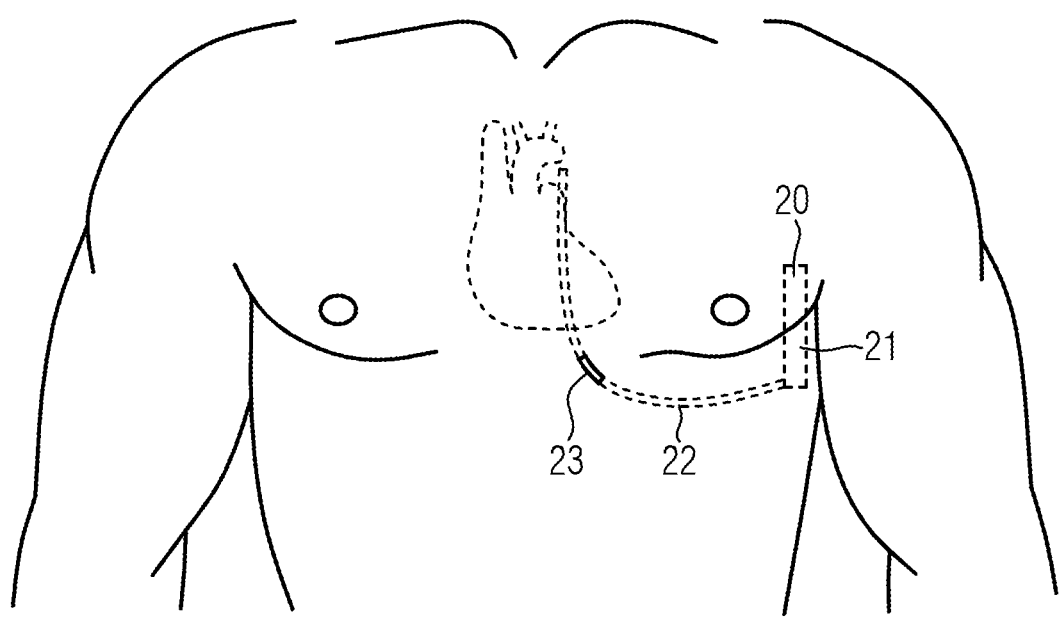
FIG. 1b represents a medical device comprising a hemodynamic cardiac sensor according to a second embodiment of the invention.
Figure 1C:
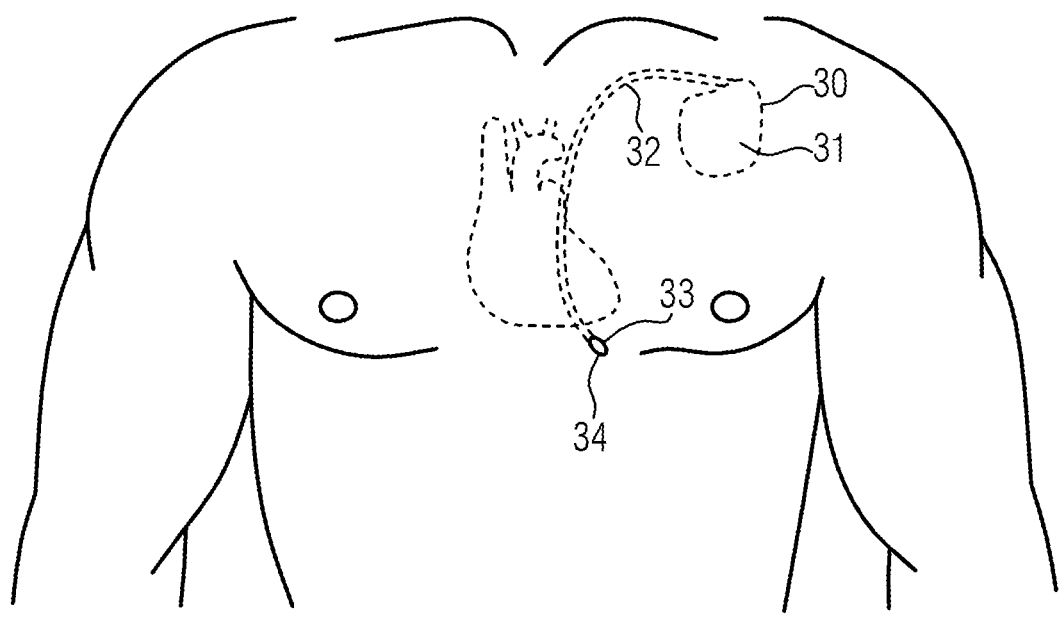
FIG. 1c represents a medical device comprising a cardiac hemodynamic sensor according to a third embodiment of the invention.

According to the present invention, the hemodynamic signals are recorded by at least one cardiac hemodynamic sensor, such as an accelerometer which can be integrated inside a defibrillator housing, in particular an implantable automatic defibrillator or in a lead connected to the defibrillator according to various embodiments (see FIGS. 1a-1c). According to an alternative embodiment, the cardiac hemodynamic sensor may be distinct from a defibrillator, that is to say not associated, not integrated or not combined with a defibrillator (see FIG. 1d).

FIG. 1a illustrates a medical device 10, in particular an implantable automatic defibrillator 10 according to a first embodiment, which is implanted subcutaneously with a mono- or multi-axis accelerometer 11 integrated at the distal end 12 of the intracardiac stimulation lead 13 of the defibrillator 10. The intracardiac stimulation lead 13 may also comprise one or more electrodes (not shown) for recording electrophysiological signals. The implantable automatic defibrillator 10 which is connected to the intracardiac stimulation lead 13, is adapted to house a microcontroller and associated electronic circuits (not shown) in a housing 14.

The medical device 10 comprises a controller (not shown) having an algorithm configured to detect ventricular fibrillation by taking into account the cardiac hemodynamic signals detected by the accelerometer 11. According to the present invention, the electrophysiological signals detected by the electrodes or the intracardiac stimulation lead 13 are not used by said algorithm of the controller. Indeed, the controller of the medical device 10 is able to detect a ventricular fibrillation episode by taking only the hemodynamic signals into account.

In addition, according to the first embodiment of the invention, the controller of the medical device 10 also comprises an algorithm configured to trigger a defibrillation operation by taking into account the hemodynamic signals. Thus, the device 10 is also configured to treat ventricular fibrillation, following the detection of a ventricular fibrillation episode, by a defibrillation signal delivered by the defibrillator 10, in particular by the intracardiac stimulation lead 13 of the defibrillator 10.

FIG. 1b illustrates a medical device 20, in particular an implantable automatic defibrillator 20 according to a second embodiment, the housing 21 of which is implanted subcutaneously under the armpit of a patient. The housing 21 of the device 20 comprises a microcontroller and associated electronic circuits (not shown) and is connected to a subcutaneous lead 22 in the parasternal region itself having one or more electrodes (not shown). Cardiac hemodynamic sensors, such as an accelerometer 23, can be integrated in the housing 21 of the device 20 and/or to the subcutaneous lead 22.

The medical device 20 comprises a controller (not shown) having an algorithm configured to detect ventricular fibrillation by taking into account the cardiac hemodynamic signals detected by the accelerometer 23. According to the present invention, the electrophysiological signals detected by the electrode(s) of the lead 22 are not used by said controller algorithm. Indeed, the controller of the medical device 20 is able to detect a ventricular fibrillation episode by taking only the hemodynamic signals into account.

In addition, according to the second embodiment of the invention, the controller of the medical device 20 also comprises an algorithm configured to trigger a defibrillation operation by taking into account the hemodynamic signals. Thus, the device 20 is also configured to treat ventricular fibrillation, following the detection of a ventricular fibrillation episode, by a defibrillation signal delivered by the defibrillator 20.

Similarly, FIG. 1c illustrates a medical device 30, particularly an implantable automatic defibrillator 30 according to a third embodiment, the housing 31 of which is subcutaneously implanted in the chest pocket. The housing 31 of the defibrillator 30 comprises a microcontroller and associated electronic circuits (not shown). The housing 31 connected to a subcutaneous stimulation lead 32 in the parasternal region itself having one or more electrodes (not shown). A hemodynamic cardiac sensor, here an accelerometer 33, is integrated at the distal end 34 of the stimulation lead 32.

The medical device 30 comprises a controller (not shown) having an algorithm configured to detect ventricular fibrillation by taking into account the cardiac hemodynamic signals detected by the accelerometer 33. According to the third embodiment of the present invention, the electrophysiological signals detected by the electrode(s) of the stimulation lead 32 are not used by said algorithm of the controller. Indeed, the controller of the medical device 30 is able to detect a ventricular fibrillation episode by taking only the hemodynamic signals into account.

According to an alternative embodiment, the electrophysiological signals that are independently detected with the hemodynamic cardiac signals are taken into account by the controller so as to compare the two types (electrophysiological and hemodynamic) of signals with each other in order to improve the reliability of the detection of a ventricular fibrillation episode.

In addition, according to the third embodiment of the invention, the controller of the medical device 30 also comprises an algorithm configured for triggering a defibrillation operation by taking into account the hemodynamic signals. So, the device 30 is also configured to treat a ventricular fibrillation following the detection of an episode of ventricular fibrillation, by a defibrillation signal delivered by the defibrillator 30, in particular of the stimulation lead 32.

Figure 1D:
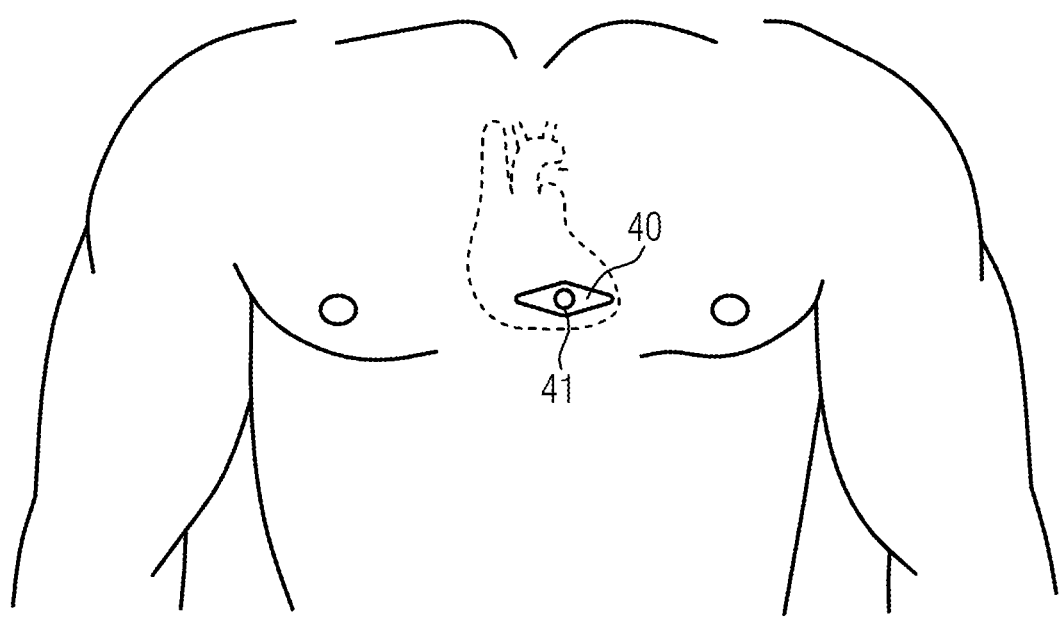
FIG. 1d represents an assembly comprising a hemodynamic cardiac sensor according to a fourth embodiment of the invention.

FIG. 1*d* illustrates a fourth embodiment wherein a cardiac hemodynamic sensor 40, in particular an accelerometer, is incorporated in the center of a bandage 41 glued to the chest of a patient. This bandage 41 may also comprise one or more electrodes (not shown), a microcontroller and associated electronic circuits (not shown). In this fourth embodiment, when ventricular fibrillation is detected by the cardiac hemodynamic sensor 40 of the bandage 41, an external defibrillator (automatic or manual) may be used for a defibrillation operation. Alternatively, the cardiac hemodynamic sensor 40 is both distinct from a defibrillator (i.e., for example, it is not integrated or connected to a defibrillator and/or to one of its pacing leads) and is not used in combination with a defibrillator.

Thus, according to the various embodiments of the invention, the hemodynamic signals are detected by at least one hemodynamic sensor, such as an accelerometer 11, 23, 33, 40 which is either implanted inside the heart 11, either subcutaneously 23, 33 or attached to the epidermis of the chest of a patient 40.

In another embodiment, the hemodynamic sensor may be a microphone, a piezoelectric sensor, a pressure sensor, or the like.

In addition, according to a variant of the invention, the recording of hemodynamic signals can be made from a combination of several hemodynamic sensors of the same type (for example several accelerometers) or of different categories (for example an implanted sensor and a skin sensor) that would be positioned at various points in a patient's body.

According to the embodiment of the invention, each of the hemodynamic sensors may be used, or not, in combination with a defibrillator, in particular an implantable defibrillator.

Whatever the embodiment of the invention, the present invention takes into account the energy required to the generation of a cardiac hemodynamic signal, such than that recorded by an accelerometer, in order to transform the signal into an alternative representation significantly facilitating the detection of ventricular fibrillation. This representation of energy is provided by the application of TEO (for "Teager Energy Operator") on the cardiac hemodynamic signal.

The Teager Energy operator (TEO in the following) is defined by the equation: TEO $\{x(n)\} = \psi(n) = x^2(n-1) - x(n-2) \cdot x(n)$ wherein "x(n)" is the input signal (in this case, the cardiac hemodynamic signal) and "$\psi(n)$" is the output signal of the operator. "n" refers a particular sample.

The TEO operator (for "Teager Energy Operator") is a mathematical operator that can be integrated into the software or hardware of an implantable cardiac device, such as an implantable automatic defibrillator, using hemodynamic sensors, such as accelerometers, to record cardiac hemodynamic signals. The sensors can be intracardiac, subcutaneous or external (i.e. with sensors attached to the patient's skin).

Figure 2:
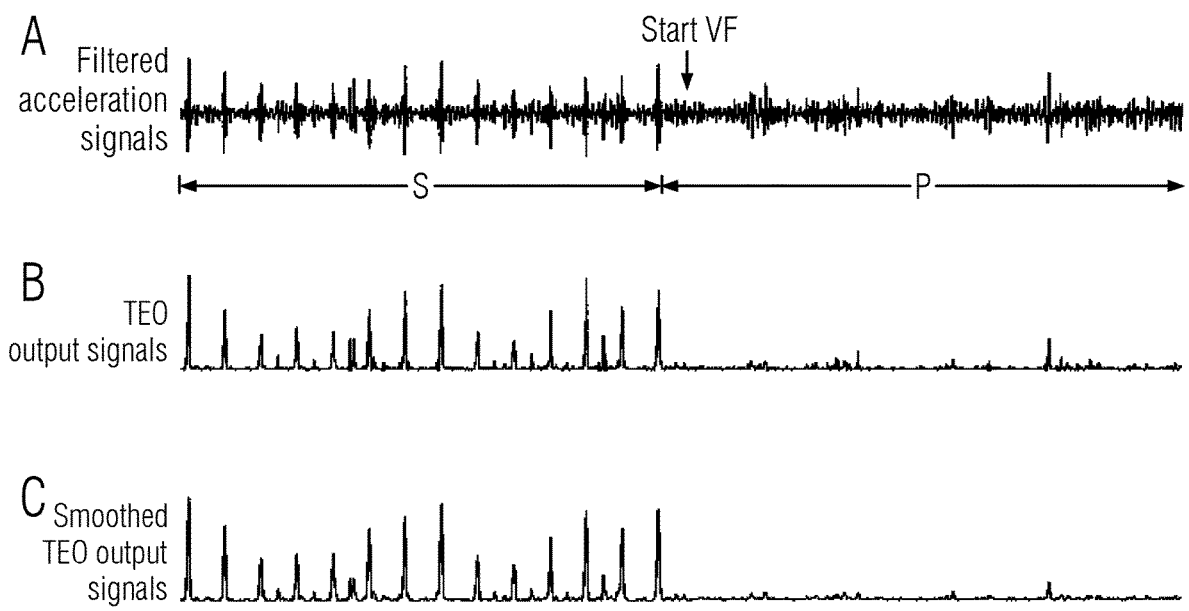
FIG. 2 represents hemodynamic signals during ventricular fibrillation.

FIG. 2 graphically represents a few seconds of a normal sinus rhythm signal before (S) and during (P) a ventricular fibrillation episode. Graph A illustrates the signal acquired by the accelerometer (A) and filtered, Graph B illustrates the TEO output signal and Graph C illustrates the smoothed TEO output signal.

The transformation of a signal by the TEO operator produces a real-time estimate of the necessary energy it took to generate the input signal. This energy is a function of the amplitude and frequency of the original signal. In particular, the energy corresponds to the weighted product of the amplitude and the frequency of the original signal. During normal sinus rhythm, the TEO output of a signal from a cardiac hemodynamic accelerometer as depicted in FIGS. 1*a*-*d* appears as a series of distinct and sharp peaks that coincide with the sounds of the heart, as illustrated by Graph A of FIG. 2. In general, the first sound of the heart, commonly called S1 sound, has greater amplitude than second sound of the heart, or S2 sound. As a result, the peak of the TEO output signal corresponding to the first cardiac sound S1 is significantly greater than that of the second S2.

Between the heart sounds S1, S2, the TEO output signal is flat as illustrated by the Graphs B and C in FIG. 2. This is due to the fact that the background noise is generally of lower amplitude and frequency relative to the sounds S1, S2 of the heart. Consequently, the transformation of a signal with the TEO operator makes it possible to considerably improve the signal-to-noise ratio of the signal in which said signal-to-noise signal corresponds to the sound S1 of the heart (caused by the turbulence caused by the closing of the mitral and tricuspid valves at the beginning of the systole) while the rest of the signal corresponds to the noise. As a result, the present invention makes it possible to improve the specificity of the discrimination of a cardiac event, in particular ventricular fibrillation.

Indeed, during a ventricular fibrillation, the synchronized and coordinated contraction of the ventricles is replaced by a disorganized or anarchic tremor. Cardiac mechanical performance is severely impaired and the ventricles do not contract with the same energy as during normal operation. This is reflected in the TEO output signal of a cardiac hemodynamic signal with a prolonged flat plateau shape close to zero and represented by the double arrow P in FIG. 2. The high amplitude characteristic peaks reflecting the heart sounds S1, S2 (see double arrow S) are absent.

As illustrated by Graph A of FIG. 2, the signals recorded with a cardiac hemodynamic sensor such as a mono- or multi-axis accelerometer, that is to say at N-axis (where N≥1), are first bandpass filtered in the 10-50 Hz frequency range, using, for example, a fourth-order Tchebychev analog filter with a 0.05% passband ripple filter (as described in the article by Weinberg, Louis, Slepian, Paul (June 1960), "Takahasi's Results on Tchebycheff and Butterworth Ladder Networks," IRE Transactions on Circuit Theory: 88-101). The filtering of hemodynamic signals in this narrow frequency band eliminates low frequency respiratory contributions as well as the contributions of high frequency acoustic heart waves. In addition, this limits the influence that motion artifacts could have on heart signals. This is particularly relevant when the patient implanted with such a device moves and, for example, does physical exercise.

After filtering, additional pre-processing can be performed on the signals recorded by the cardiac hemodynamic sensor. For example, the signals can be analyzed independently and sorted by valuable order. Such a classification could take into account amplitude, frequency, signal-to-noise ratio, stability or signal sensitivity in response to a hemodynamic change. A selection of signals can also be considered. The best signal according to the ranking criteria can be selected for a subsequent processing.

Alternatively, the signals may be combined in some way to produce a different, more specific signal for the detection of ventricular fibrillation.

Figure 3:
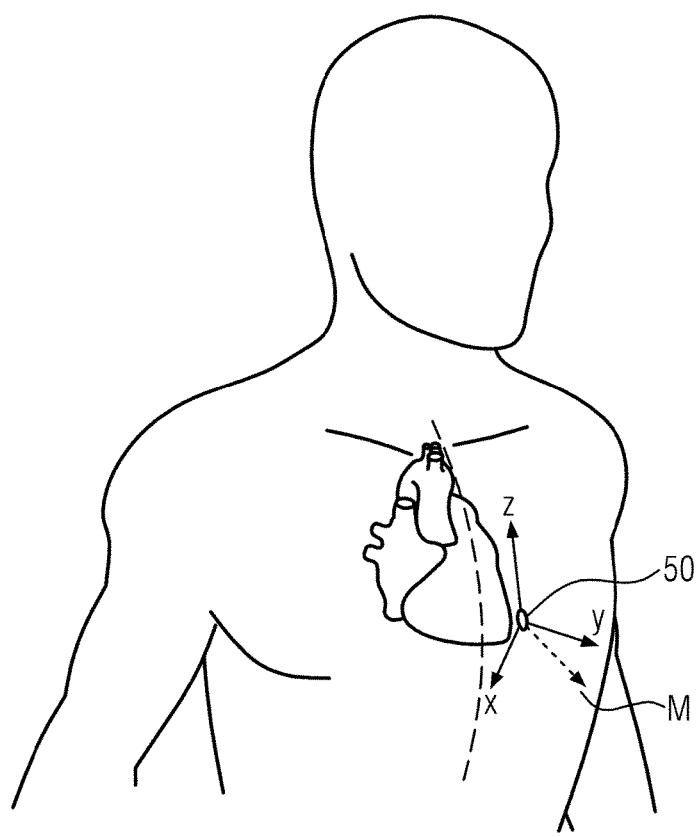
FIG. 3 represents a three-axis accelerometer.

FIG. 3 represents a 3-axis (x, y, z) accelerometer 50 that could be integrated in one of the devices 10, 20, 30 or be the hemodynamic sensor 40. The cardiac systolic mechanical axis M, shown in FIG. 3, is the axis parallel to the maximum force vector generated by the heart during normal contraction. The components of the original hemodynamic signals along the x, y, z axes are projected along this cardiac systolic mechanical axis M and summed to produce a new signal. The cardiac hemodynamic signal recorded along this axis M indicates the maximum amplitude and substantially the maximum signal-to-noise ratio that can be recorded by a hemodynamic sensor, such as an accelerometer, at the position illustrated in FIG. 3 a signal along this cardiac mechanical axis M is substantially a signal which is more physiological, patient-specific and thus less arbitrary than a signal simply recorded along the anteroposterior axis, for example.

After filtering and preprocessing, the hemodynamic signal serves as an input signal to the TEO. Before being capable of detecting a ventricular tachyarrhythmia such as ventricular fibrillation according to several embodiments of the algorithm, the TEO output signal is smoothed with, for example, a Hamming window, as shown in Graph C of FIG. 2. The Hamming window makes it possible to make the peaks of the output signals larger compared to the noise but also to facilitate the processing of the output signals for several embodiments of the algorithm, because it reduces the risk of double detections (i.e. several peaks located close to each other and being possibly mistaken as a single peak).

After filtering, preprocessing and smoothing, the smoothed TEO output signals serve as input to algorithms that take into account the frequency and/or amplitude of the TEO output signals in order to detect the presence of a ventricular tachyarrhythmia such as ventricular fibrillation. Several embodiments of these algorithms are described in the following.

Figure 4A:
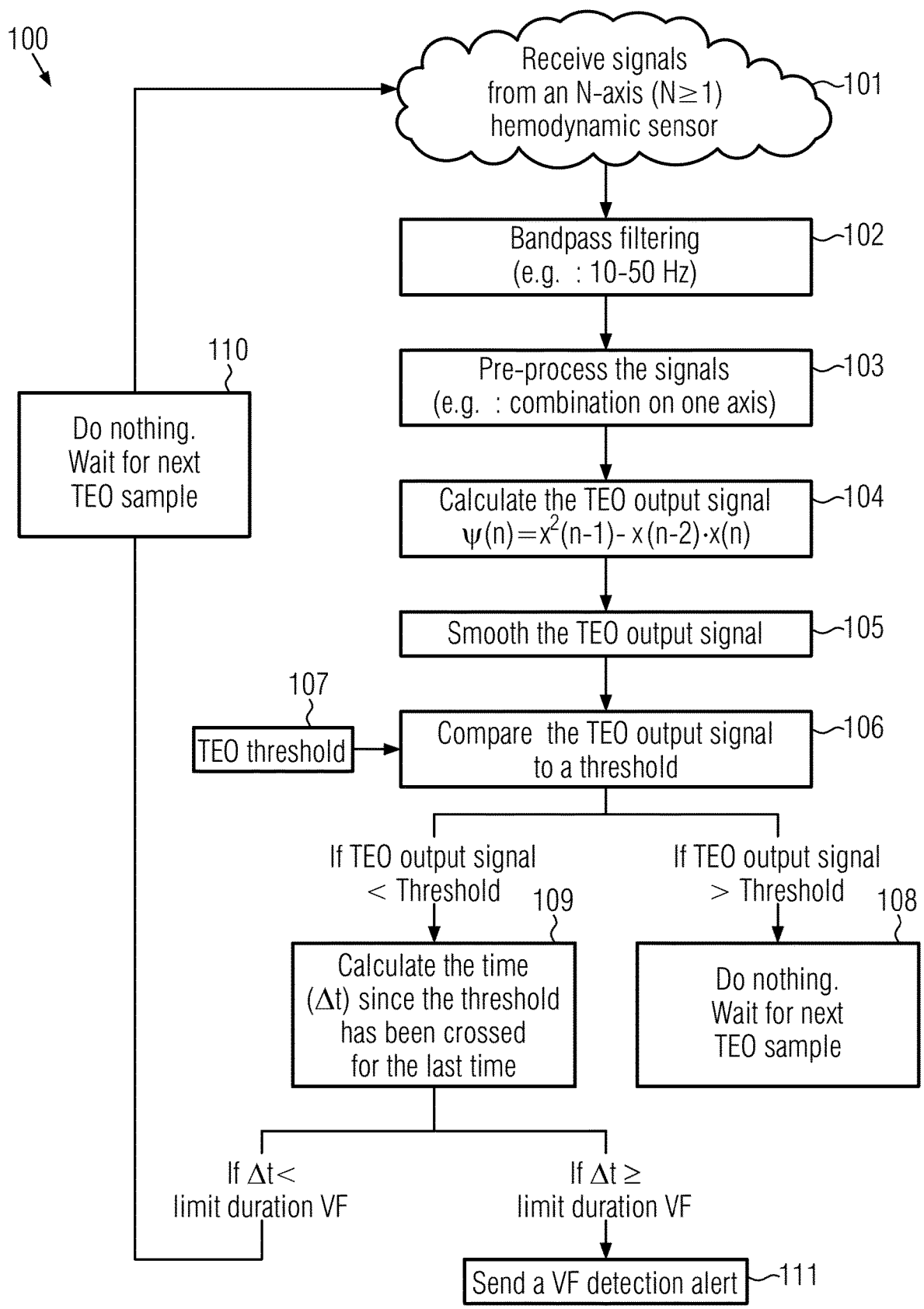
FIG. 4a represents an algorithm according to a first embodiment of the invention.

FIG. 4a illustrates a first embodiment of an algorithm 100.

At step 101, a sample n of hemodynamic signals recorded by a hemodynamic sensor is received. The hemodynamic sensor may be an accelerometer, a microphone, a piezoelectric sensor, a pressure sensor or the like. In addition, according to a variant of the invention, the recording of hemodynamic signals can be made from a combination of several hemodynamic sensors of the same type (for example several accelerometers) or of different categories (for example an implanted sensor and a skin sensor) that would be positioned at various points in a patient's body.

In step 102, the hemodynamic signals are bandpass filtered in the 10-50 Hz frequency range to eliminate low frequency respiratory contributions and high frequency acoustic cardiac wave contributions.

In step 103, the signals are preprocessed to make them more relevant for the detection of ventricular fibrillation. Such preprocessing has been described with reference to FIGS. 2 and 3. For example, in the case wherein the hemodynamic sensor is an N-axis accelerometer, the components of the hemodynamic signals along the N-axes can be projected and added along an N+1 axis, in particular along the systolic cardiac mechanical axis M to produce a new signal whose amplitude is maximized. Alternatively or in combination, the signals may be bandpass filtered in the 1050 Hz frequency range, using for example, a fourth order Tchebychev analog filter with a 0.05% bandpass ripple filter.

Filtered and preprocessed cardiac hemodynamic signals are then used as input signals in the TEO operator. At a step 104, the hemodynamic signals are transformed by application of the TEO operator that provides a real time estimate of the energy needed to produce these signals. This energy is a function of the amplitude and frequency of the original signal. In particular, the energy corresponds to the weighted product of the amplitude and the frequency of the original signal.

In a step 105, the TEO output signals are smoothed, for example, by applying a Hamming window.

In step 106, the smoothed TEO output signals are compared with a threshold value 107. This threshold value 107 can be a static value (i.e. a single constant value calculated and defined a priori) or a dynamic value (i.e. it is regularly recalculated using various values of the original or processed signal). According to the embodiment wherein several cardiac hemodynamic signals are recorded by different hemodynamic sensors, for example by a first implanted sensor and by a second skin sensor, the threshold value can be calculated by crossing and verifying the hemodynamic signals of the first and second hemodynamic sensors. In another embodiment wherein the cardiac hemodynamic signals are recorded by an N-axis hemodynamic sensor (see the example shown in FIG. 3), the threshold value can be calculated by crossing and checking the hemodynamic signals respectively recorded along each axis.

If the TEO output signal is greater than the threshold value 107, no action is taken in step 108 and the next sample of smoothed TEO output signals is ready to be taken into account. If, however, the TEO output signal is less than the threshold value 107, the elapsed time "At" between the current sample and the last sample which has been greater than the threshold 107 is calculated at a step 109.

If the elapsed time "At" is less than a specific time limit that is characteristic of a ventricular fibrillation ("limit duration VF" in FIG. 4a), at step 110 no action is taken and the reception of the next n+1 sample of TEO output signals is expected.

If, however, the elapsed time "At" is greater than or equal to the "limit duration VF", a ventricular fibrillation is detected and an alert is triggered in step 111. As for the threshold, the specific value of the "VF limit duration" may also be a static value (i.e. a single, unchanged and defined a priori value) or a dynamic value (i.e. it is regularly recalculated according to the original signal or to the output signal).

Figure 4B:
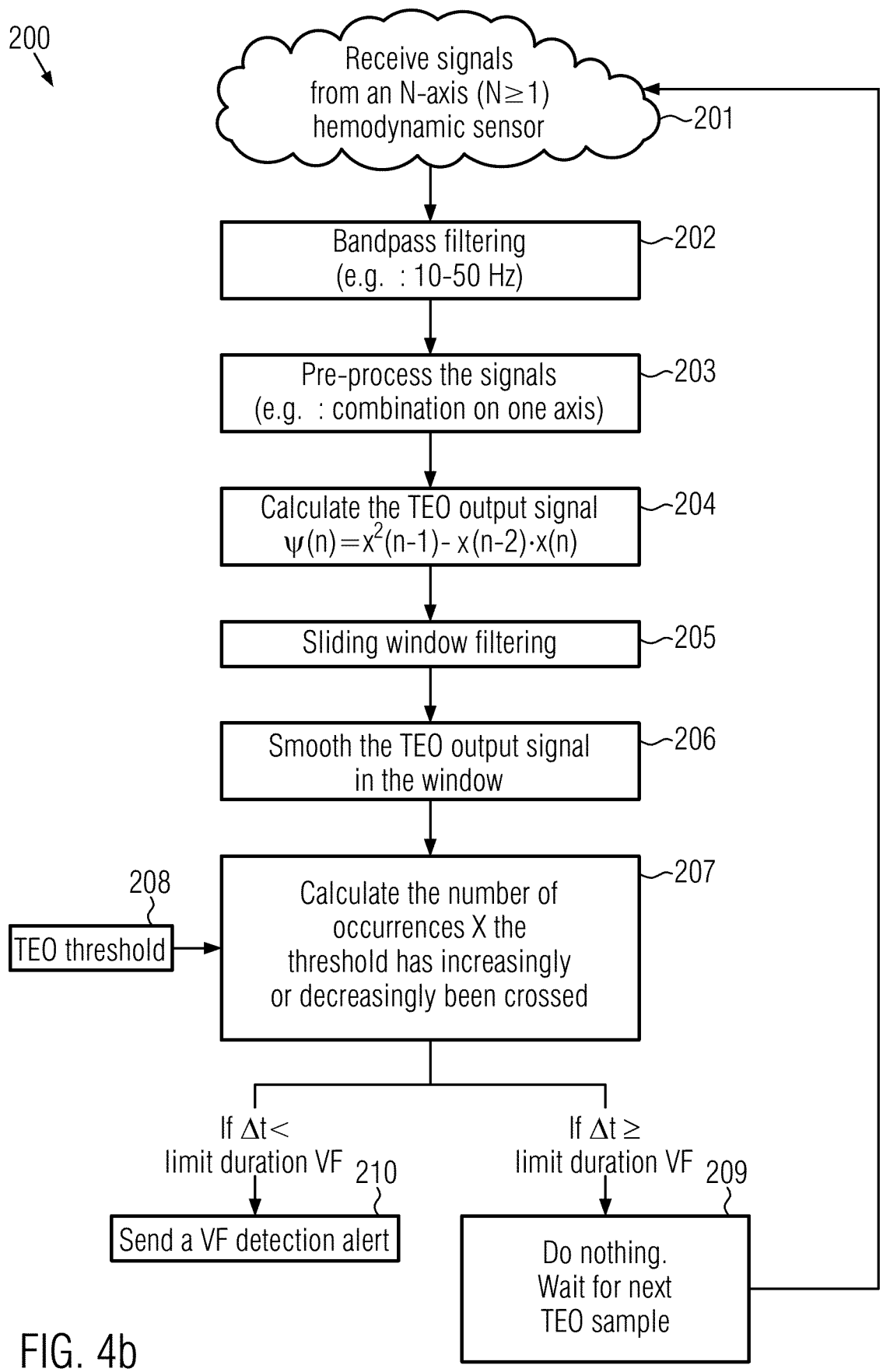
FIG. 4b represents an algorithm according to a second embodiment of the invention.

FIG. 4b illustrates a second embodiment of an algorithm 200.

In a method similar to algorithm 100, a sample n of hemodynamic signals recorded by a hemodynamic sensor is received in step 201. The hemodynamic sensor may be an accelerometer, a microphone, a piezoelectric sensor, a pressure sensor, or the like. In addition, according to a variant of the invention, the recording of hemodynamic signals can be made from a combination of several hemodynamic sensors of the same type (for example several accelerometers) or of different categories (for example an implanted sensor and a skin sensor) that would be positioned at various points in a patient's body.

Then, at step 202, the hemodynamic signals are bandpass filtered in the 10-50 Hz frequency range to eliminate low frequency respiratory contributions and high frequency acoustic cardiac wave contributions.

In step 203, the signals are preprocessed to make them more relevant for the detection of ventricular fibrillation. Such preprocessing has been described with reference to FIGS. 2, 3 and 4a. At a step 204, the hemodynamic signals are transformed by application of the TEO operator.

According to the second embodiment, in a step 205, the TEO output signals are filtered by applying a sliding window filter whose "window" length can be a static value (i.e. a single value unchanged calculated and defined a priori) or a dynamic value (i.e. it is regularly recalculated using the original or output signal).

The "window" is slided (i.e. moved to the next or previous sample without "jumping" more than one sample at a time, as is the case with "jumping windows"), on the last sample of TEO output signals that are smoothed at a step 206 using, for example, a Hamming window.

At a step 207, the smoothed TEO output signals are compared to a threshold value 208 within the "window". This threshold value 208 can be a static value (i.e. a single unchanged value calculated and defined a priori) or a dynamic value (i.e. it is regularly recalculated using the output signal TEO smooth). In step 207, the number of times X that the threshold 208 has been crossed in either increasing or decreasing order or the number of peaks X exceeding the threshold 208 within the "window" is calculated.

If the number X is greater than a specific limit number ("Limit VF" in FIG. 4b), in step 209 no action is taken and the receipt of the next n+1 sample of signals is expected.

If the number X is less than the specific limit number "limit VF", a ventricular fibrillation is detected and an alert is triggered in step 210. As for threshold 208, the specific value of the number "limit VF" can also be a static value (i.e. a single, unchanged and defined a priori value) or a dynamic value (i.e. that it is regularly recalculated according to the original signal or the output signal).

According to the embodiment wherein several cardiac hemodynamic signals are recorded by different hemodynamic sensors, for example by a first implanted sensor and by a second skin sensor, the threshold value can be calculated by crossing and verifying the hemodynamic signals of the first and second hemodynamic sensors.

According to another embodiment wherein the cardiac hemodynamic signals are recorded by an N-axis hemodynamic sensor (see the example shown in FIG. 3), the threshold value can be calculated by crossing and verifying the hemodynamic signals respectively recorded along each axis.

Figure 4C:
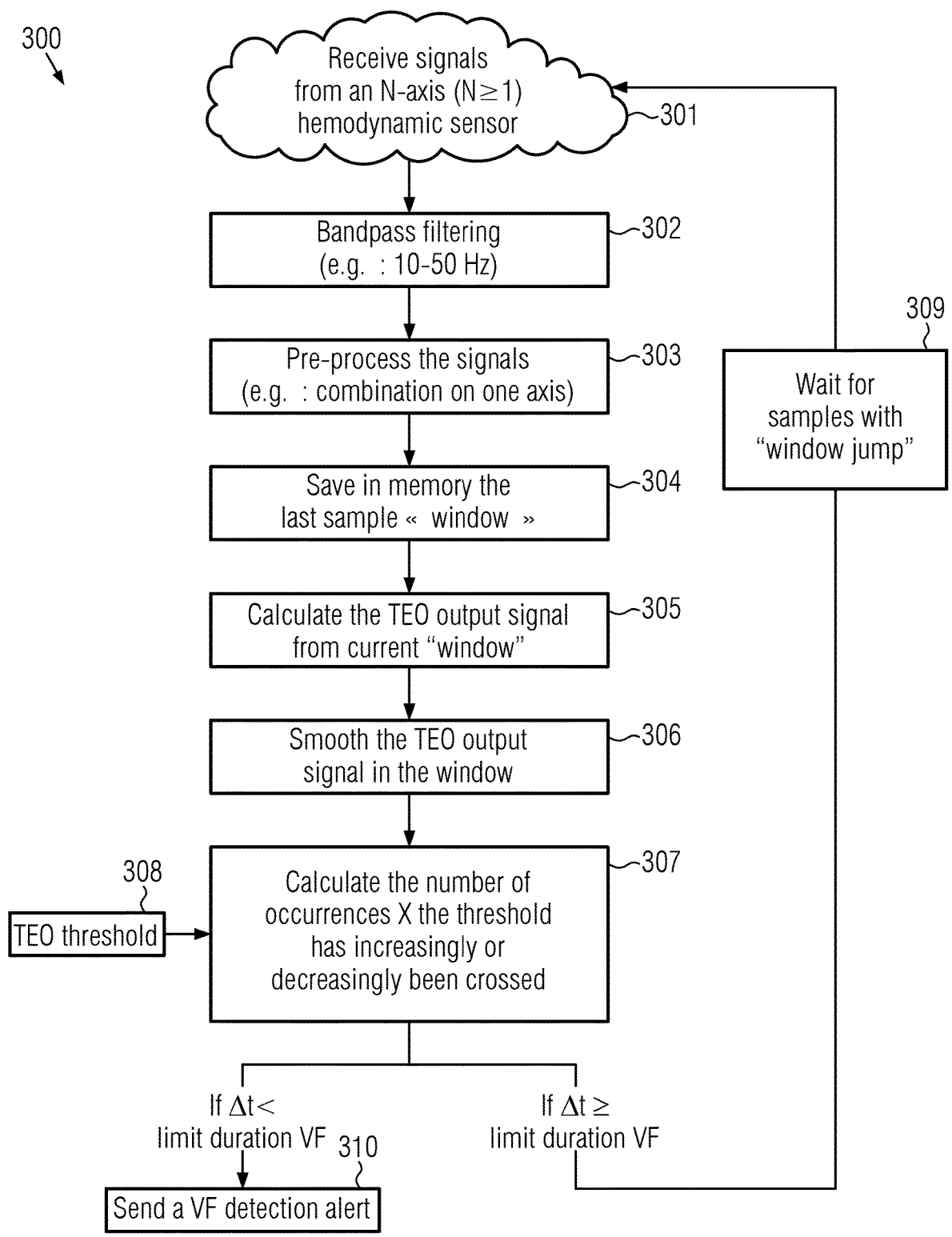
FIG. 4c represents an algorithm according to a third embodiment of the invention.

FIG. 4c illustrates a third embodiment of an algorithm 300.

In a similar method to the algorithm 200, a sample n of hemodynamic signals recorded by a hemodynamic sensor is received at a step 301. The hemodynamic sensor may be an accelerometer, a microphone, a piezoelectric sensor, a pressure sensor, or the like. In addition, according to a variant of the invention, the recording of hemodynamic signals can be made from a combination of several hemodynamic sensors of the same type (for example several accelerometers) or of different categories (for example an implanted sensor and a skin sensor) that would be positioned at various points in a patient's body.

Then, in step 302, the hemodynamic signals are bandpass filtered in the 10-50 Hz frequency range to eliminate low frequency respiratory contributions and high frequency acoustic cardiac wave contributions.

In step 303, the signals are preprocessed to make them more relevant for the detection of ventricular fibrillation. Such preprocessing has been described with reference to FIGS. 2, 3 and 4a.

According to the third embodiment, in step 304, after band pass filtering and preprocessing, the last samples of the cardiac hemodynamic signal of the "window" are stored in the memory. This window is of the "jumping window" type and the length of the "window" can be a static value (i.e. a single unchanged value, calculated and defined a priori) or a dynamic value (i.e. it is regularly recalculated using the original or output signal).

At a step 305, the hemodynamic signals are transformed by application of the TEO operator. In step 305, the TEO output signals are calculated in the current "window".

At a step 306, the TEO output signals are smoothed in the current "window" using for example, a Hamming window.

At a step 307, the smoothed TEO output signals are compared to a threshold value 308 within the "window". This threshold value 308 can be a static value (i.e. a single unchanged value, calculated and defined a priori) or a dynamic value (i.e. it is regularly recalculated using the smoothed TEO output signal).

According to the embodiment wherein several cardiac hemodynamic signals are recorded by different hemodynamic sensors, for example by a first implanted sensor and by a second skin sensor, the threshold value can be calculated by crossing and verifying the hemodynamic signals of the first and second hemodynamic sensors.

According to another embodiment wherein the cardiac hemodynamic signals are recorded by an N-axis hemodynamic sensor (see the example represented by FIG. 3), the threshold value can be calculated by crossing and checking the hemodynamic signals respectively recorded along each axis.

In step 307, the number of times X that the threshold 308 has been crossed in either increasing or decreasing order, or the number of peaks X exceeding the threshold 308 within the "window" is calculated.

If the number X is greater than a specific limit number ("limit VF" in FIG. 4c) no ventricular fibrillation has been detected: at step 309 the algorithm 300 waits for a specific number of "sample jumps" before considering the processing of the next window. Meanwhile, the preprocessed signal is still being recorded and saved in memory at step 304 to be taken into account in the next window.

If the number X is less than the specific limit number "limit VF", a ventricular fibrillation is detected and an alert is triggered in step 310. As for threshold 308, the specific value of the "limit VF" number can also be a static value (i.e. a single value, unchanged and defined a priori) or a dynamic value (i.e. it is regularly recalculated according to the original signal or the output signal).

The algorithm 300 allows a computation cost lower than that of the algorithms 100 and 200 because it calculates only the TEO output signal within the window for all "sample jumps" rather than continuously.

Figure 4D:
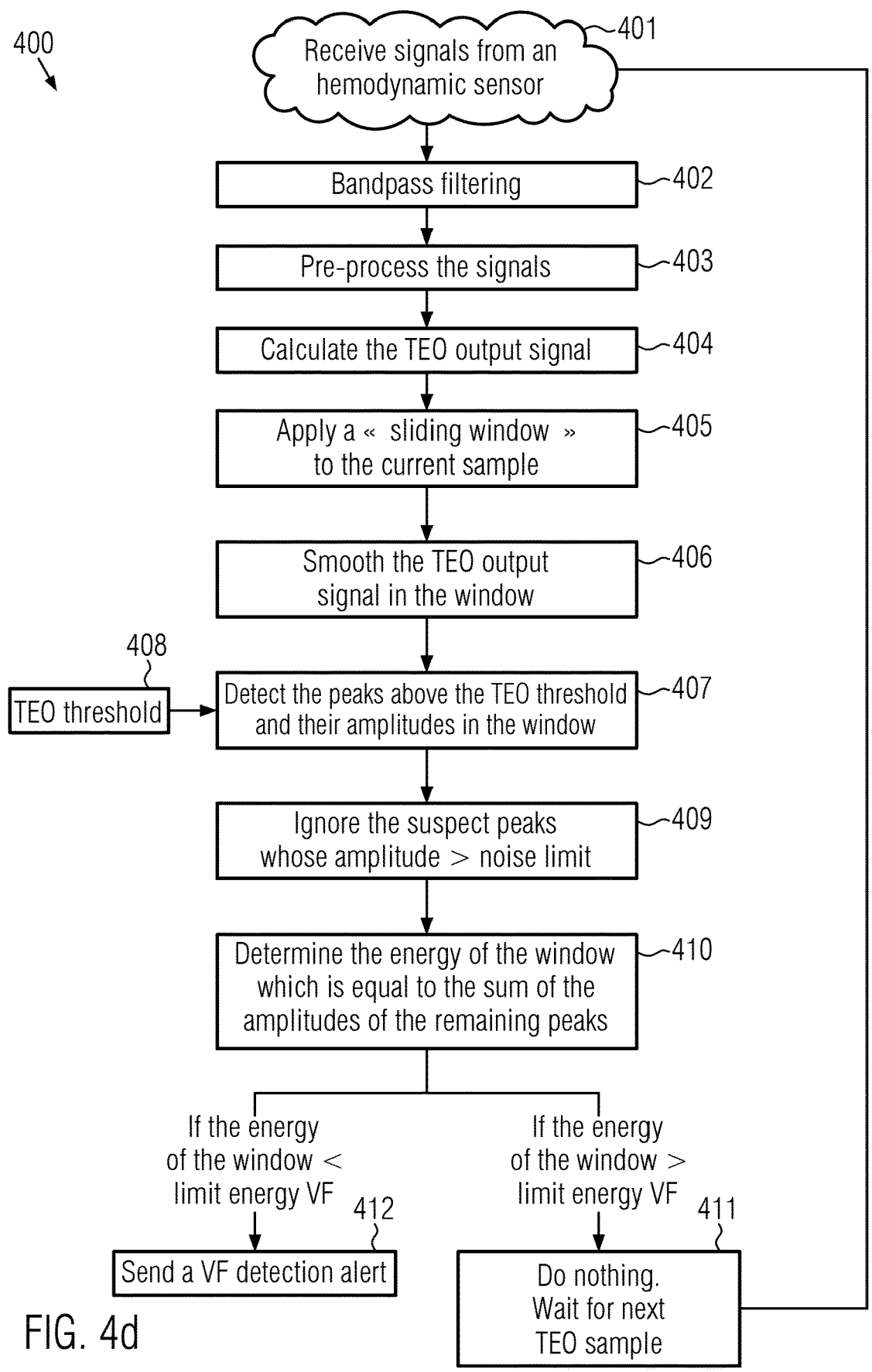
FIG. 4d represents an algorithm according to a fourth embodiment of the invention.

FIG. 4d illustrates a fourth embodiment of an algorithm 400.

Unlike the previous algorithms 100, 200, 300, the algorithm 400 takes into account the number of peaks exceeding the threshold in a "sliding window" or a "jumping window", as well as their amplitudes.

At a step 401, a sample n of hemodynamic signals recorded by a hemodynamic sensor is received. The hemodynamic sensor may be an accelerometer, a microphone, a piezoelectric sensor, a pressure sensor or the like. In addition, according to a variant of the invention, the recording of hemodynamic signals can be made from a combination of several hemodynamic sensors of the same type (for example several accelerometers) or of different categories (for example an implanted sensor and a skin sensor) that would be positioned at various points in a patient's body.

Then, at step 402, the hemodynamic signals are bandpass filtered in the 10-50 Hz frequency range to eliminate low frequency respiratory contributions and high frequency acoustic wave contributions.

In step 403, the signals are preprocessed to make them more relevant for the detection of ventricular fibrillation. Such preprocessing has been described with reference to FIGS. 2, 3 and 4a.

At a step 404, the hemodynamic signals are transformed by application of the TEO operator.

According to the fourth embodiment, the output signals TEO are considered in a "sliding" window in step 405. The value of the length of the window can be a static value (i.e. a constant value, calculated and defined a priori) or a dynamic value (i.e. it is regularly recalculated using the original or processed signal).

In step 406, the TEO output signals are smoothed in said window using, for example, a Hamming window.

In step 407, the peaks of the smoothed TEO output signals exceeding a TEO threshold value 408 in the window and their amplitudes are determined. This threshold value 408 can be a static value (i.e. a single unchanged value calculated and defined a priori) or a dynamic value (i.e. it is regularly recalculated using the output signal TEO smooth).

According to the embodiment wherein several cardiac hemodynamic signals are recorded by different hemodynamic sensors, for example by a first implanted sensor and a second skin sensor, the threshold value can be calculated by crossing and verifying the hemodynamic signals of the first and second hemodynamic sensors.

According to another embodiment wherein the cardiac hemodynamic signals are recorded by an N-axis hemodynamic sensor (see the example shown in FIG. 3), the threshold value can be calculated by crossing and checking the hemodynamic signals respectively recorded along each axis.

Peaks with particularly large amplitudes are suspected to be external and parasitic noises and could then mislead signal processing. Therefore, in step 409, all peaks whose amplitude exceeds a specific value ("noise limit" in FIG. 4d) are ignored. The value of "noise limit" can be a static value (i.e., a single unchanged value, calculated and defined a priori) or a dynamic value (i.e. it is regularly recalculated using the smoothed TEO output signal).

In step 410, the amplitudes of the remaining peaks are summed to give only one value called "window energy".

If the value of "window energy" is greater than a specific value called "limit energy VF", in step 411 no action is taken and the receipt of the next n+1 signal sample is expected.

If the value of "window energy" is less than said specific value "limit energy VF", a ventricular fibrillation is detected and an alarm is triggered at step 412. As for threshold 408, the specific value of the "limit energy VF" number can also be a static value (i.e. a single value, unchanged and defined a priori) or a dynamic value (i.e. it is regularly recalculated according to the original or to the output signal). This threshold "limit energy VF" can be interpreted as the minimum energy required to ensure a sufficient systemic infusion (i.e. blood circulation in the brain and body).

The different embodiments of the device and method 100, 200, 300, 400 according to the present invention may further be configured to trigger a defibrillation operation following the detection of ventricular fibrillation, following the steps of "VF detection alert" 111, 210, 310, 412, in particular by a manual or automatic defibrillator. In addition, the method and device of the present invention may be configured to verify that the defibrillation operation has been effective, i.e. whether or not the mechanical activity of the heart has been reestablished after defibrillation operation. To do this, after a predetermined lapse of time allowing the recovery of the normal heart rate following the defibrillation operation, a hemodynamic cardiac signal is detected by a hemodynamic sensor and is processed in particular by the application of the TEO operator, as described with respect to FIGS. 4a to 4d. A "post-processing" output hemodynamic cardiac signal is thus defined. In the same method as described with respect to at least one of FIGS. 4a to 4d, said "post-processing" output hemodynamic cardiac signal is compared to a predetermined threshold to determine if the defibrillation operation has been effective in treating ventricular fibrillation. In the negative case, a new defibrillation operation may be initiated during which a therapeutic electrical defibrillation signal (electric shock) is delivered to the patient.

The described embodiments are merely possible configurations and it should be kept in mind that the individual features of the different embodiments may be combined with each other or provided independently of one another.

In addition, each of the algorithms 100, 200, 300, 400 may comprise additional steps before, between, or after the steps that have been described with reference to FIGS. 4a, 4b, 4c and 4d.

What is claimed is:

1. A medical device comprising:
   at least one implantable or non-implantable hemodynamic sensor configured to detect hemodynamic cardiac signals; and
   a controller configured to process and analyze the detected hemodynamic cardiac signals or signals derived from detected hemodynamic cardiac signals by applying to said signals a Teager Energy Operator (TEO) defined by:
   TEO $\{x(n)\} = \psi(n) = x^2(n-1) - x(n-2) \cdot x(n)$
   wherein "x(n)" is a cardiac hemodynamic signal,
   "$\psi(n)$" is the output hemodynamic signal and
   "n" refers to a predetermined sample,
   said controller further comprising instructions configured to implement at least one algorithm that determines the need for a defibrillation operation by taking into account the at least one output hemodynamic signal.

2. The medical device of claim 1, wherein the at least one hemodynamic sensor is an implantable or non-implantable accelerometer, a microphone, a piezoelectric sensor or a pressure sensor able to detect hemodynamic cardiac signals, in particular heart sounds.

3. The medical device of claim 1, wherein the at least one algorithm of the controller is configured to determine the need for a defibrillation operation if at least one characteristic of the output hemodynamic signals does not exceed a predetermined threshold during a lapse of time that is greater than a duration associated with a ventricular fibrillation episode.

4. The medical device of claim 3, wherein the at least one characteristic of the output hemodynamic signal is the amplitude, the energy, the average value, the median value, or the root mean square value of said signal.

5. The medical device of claim 3, wherein the amplitude of the output hemodynamic signals, the number of times that each of the output hemodynamic signals crosses in either ascending or descending order the predetermined threshold, or the number of peaks of each signal that exceeds the predetermined threshold during the predefined time lapse are taken into account for determining the presence or absence of ventricular fibrillation.

6. The medical device of claim 1, further comprising a defibrillator, in particular an implantable defibrillator, configured to generate an electrical defibrillation signal, and at least one electrode connected to said defibrillator by a lead configured to deliver said electrical defibrillation signal to a patient when the need to initiate a defibrillation operation is determined by the controller of the medical device.

7. The medical device of claim 6, wherein the controller is configured to determine the need for initiating a defibrillation operation by comparing the output hemodynamic signal signals with at least one electrophysiological signal independently detected from the cardiac hemodynamic signals by the at least one electrode.

8. The medical device of claim 6, wherein the controller is configured to determine the need for a defibrillation operation by taking into account only cardiac hemodynamic signals.

9. The medical device of claim 1, wherein the controller is configured to bandpass filter the detected cardiac hemodynamic signals or signals derived from detected cardiac hemodynamic signals in a range of 7.5 to 49 Hz.

10. The medical device of claim 9, wherein the controller is further configured to filter the output signals by applying a windowing function, in particular a Hamming window.

11. The medical device of claim 10, wherein the controller is configured to determine the need for a defibrillation operation or for initiating a defibrillation operation according to a predefined static threshold or a dynamic threshold, recalculated periodically and derived from one or more characteristics of the cardiac hemodynamic signals or from their representation by the Teager Energy Operator.

12. A method for treating hemodynamic cardiac signals detected by at least one hemodynamic sensor of a medical device, comprising:
  processing, by a controller of the medical device, the detected hemodynamic signals or signals derived from the detected hemodynamic cardiac signals which comprises applying a Teager Energy Operator (TEO) defined by:
  TEO $\{x(n)\} = \psi(n) = x^2(n-1) - x(n-2) \cdot x(n)$
  wherein "$x(n)$" is a detected cardiac hemodynamic signal;
  "$\psi(n)$" is the output hemodynamic cardiac signal; and
  "$n$" refers to a predetermined sample,
  determining, by the controller of the medical device, the presence or absence of ventricular fibrillation by taking into account the output hemodynamic signal relative to a predetermined threshold; and
  providing a therapy responsive to determining the presence of ventricular fibrillation.

13. The method for treating hemodynamic cardiac signals of claim 12, wherein the signal processing step is preceded by a signal preprocessing step, processed by the controller of the medical device, at which the detected hemodynamic signals or signals derived from the detected cardiac hemodynamic signals are bandpass filtered, in particular in a range of 7.5 to 49 Hz.

14. The method for treating cardiac hemodynamic signals of claim 12, wherein the signal processing step is followed by a signal post-processing step, processed by the controller of the medical device, during which the output hemodynamic signals are filtered by application of a windowing function, in particular by applying a Hamming window.

15. The method for treating cardiac hemodynamic signals of claim 12, wherein the at least one hemodynamic sensor is an implantable or non-implantable N-axis accelerometer (N$>=$1), a microphone, a piezoelectric sensor or a pressure sensor adapted to detect cardiac hemodynamic signals, in particular heart sounds.

16. The method for treating cardiac hemodynamic signals of claim 15, wherein the N cardiac signals detected by the N-axis accelerometer are combined in a new signal along an N+1 axis, the N+1 axis being determined so that the amplitude, the signal-to-noise ratio, the stability, or a relevant physiological parameter of the new signal is maximum along the N+1 axis.

17. The method for treating cardiac hemodynamic signals of claim 12, wherein the predetermined threshold is a predefined static threshold, or a dynamic threshold, recalculated periodically and derived from one or more characteristics of the cardiac hemodynamic signals or their representation by the Energy Operator Teager.

18. The method for treating hemodynamic cardiac signals of claim 12, wherein the amplitude, the number of times each of the output hemodynamic signals crosses in either ascending or descending order the predetermined threshold, or the number of peaks of each signal that exceeds the predetermined threshold for a predefined period of time, is/are taken into account for determining the presence or absence of ventricular fibrillation.

19. The method for treating cardiac hemodynamic signals according to claim 12, wherein the presence or absence of ventricular fibrillation is determined by taking into account only cardiac hemodynamic signals.

20. The method for treating hemodynamic cardiac signals according to claim 12, wherein the presence or absence of ventricular fibrillation is established by comparing the output hemodynamic signal with at least one electrophysiological signal detected by an electrode of the medical device.

21. One or more non-transitory computer-readable storage media having instructions stored thereon for the processing of hemodynamic cardiac signals detected by at least one hemodynamic sensor of a medical device that, upon execution by one or more processors, cause the one or more processors to perform operations comprising:
  processing detected hemodynamic signals or signals derived from detected cardiac hemodynamic signals by application of a Teager Energy Operator (TEO) defined by:
  TEO $\{x(n)\} = \psi(n) = x^2(n-1) - x(n-2) \cdot x(n)$
  wherein "$x(n)$" is the detected hemodynamic signal,
  "$\psi(n)$" is the output signal, and
  "$n$" refers to a predetermined sample; and
  comparing at least one characteristic of the output signal to a predetermined threshold; and triggering an alert when the at least one characteristic of the output signal does not exceed the predetermined threshold for a predefined period of time.

22. The one or more non-transitory computer-readable media of claim 21, wherein the operations further comprise preprocessing the detected cardiac hemodynamic signals or signals derived from the cardiac hemodynamic signals detected by bandpass filtration in a range of 7.5 to 49 Hz.

23. The one or more non-transitory computer-readable media of claim 21, wherein the operations further comprise post processing the output signal by applying a Hamming window function.

* * * * *